United States Patent [19]
van der Veen

[11] Patent Number: 5,531,771
[45] Date of Patent: Jul. 2, 1996

[54] DUAL CHAMBER PACEMAKER SYSTEM AND METHOD WITH IMPROVED SWITCHING BETWEEN SYNCHRONOUS AND ASYNCRHONOUS BEHAVIOR

[75] Inventor: Johannes S. van der Veen, Dieren, Netherlands

[73] Assignee: Vitatron Medical, B.V., Dieren, Netherlands

[21] Appl. No.: 329,232

[22] Filed: Oct. 26, 1994

[51] Int. Cl.⁶ .................................................. A61N 1/36
[52] U.S. Cl. ............................................................ 607/9
[58] Field of Search .................................... 607/9, 14, 25

[56] References Cited

U.S. PATENT DOCUMENTS

| | | | |
|---|---|---|---|
| 4,429,697 | 2/1984 | Nappholz et al. | 607/9 |
| 4,467,807 | 8/1984 | Bornzin . | |
| 4,527,568 | 7/1985 | Rickards . | |
| 4,539,991 | 9/1985 | Boute et al. . | |
| 4,554,921 | 11/1985 | Boute et al. . | |
| 4,920,965 | 5/1990 | Funke et al. . | |
| 4,951,667 | 8/1990 | Markowitz et al. . | |
| 5,065,759 | 11/1991 | Begemann et al. . | |
| 5,247,930 | 9/1993 | Begemann et al. | 607/11 |
| 5,342,405 | 8/1994 | Duncan | 607/9 X |

FOREIGN PATENT DOCUMENTS

0360668 3/1990 European Pat. Off. ............. 607/9

*Primary Examiner*—William E. Kamm
*Assistant Examiner*—Jeffrey R. Jastrzab
*Attorney, Agent, or Firm*—Woodcock Washburn Kurtz Mackiewicz & Norris

[57] ABSTRACT

A dual chamber pacemaker system having a dynamic tracking limit, as well as a dynamic pacing limit (flywheel rate), the two dynamic limits being normally coupled to a measure of the sensed atrial rate as long as such rate is physiological. When the atrial signal is lost, i.e., cannot be tracked, the pacemaker responds with asynchronous pacing and normally decrements both dynamic limits, taking the flywheel rate down toward a lower pacing limit. The pacemaker of this invention provides a freeze function whereby the dynamic pacing limit and dynamic tracking limit are maintained constant for a plurality of cycles following asynchronous operation, to improve the possibility of regaining tracking if an underlying physiological atrial signal reappears at about the rate prior to being lost. The freeze function may be timed out for a predetermined number of cycles, e.g., eight, or may have a reduced duration if a series of consecutive synchronous cycles is detected. In a second embodiment, the dynamic tracking limit is decreased without any freeze when the pacer goes into asynchronous operation, but the dynamic tracking limit which existed just before the switch to asynchronous operation is remembered; if the atrial rate reappears below this remembered dynamic tracking limit, the dynamic tracking limit is ramped upward to achieve quick tracking of the reappeared sinus rate. A further embodiment may incorporate the features of the first two embodiments, i.e., a short freeze followed by a period of remembering the value of DTL when async mode was initiated.

14 Claims, 9 Drawing Sheets

DUAL CHAMBER PACEMAKER SYSTEM AND METHOD WITH IMPROVED SWITCHING BETWEEN SYNCHRONOUS AND ASYNCRHONOUS BEHAVIOR

BACKGROUND OF THE INVENTION

1. Field of the Invention

This invention relates to cardiac pacing systems and, more particularly, to dual chamber pacing systems designed to optimize operation in a synchronous tracking mode.

2. Description of the Prior Art

The advantages of dual chamber pacing, and more particularly pacing in different modes which are selected in response to different patient conditions, is now well recognized in the art. Early pacing systems were solely ventricular, and were sufficient for management of patients with complete heart block and Stokes-Adams attacks. However, ventricular demand pacemakers are not equipped to take advantage of atrial activity, and thus are limited in their efficiency. Subsequently, atrial synchronous, ventricular pacemakers were introduced, having a lead for sensing P signals from the atrium and another for pacing the ventricle after a suitable P-R (A-V) interval. Such a pacemaker, e.g. VDI or VDD, allows the atrium to control the heart's response rate, the ventricle being paced at the atrial rate up to a predetermined upper rate limit. Such synchronous pacers have incorporated means for dealing with high atrial rates, including "block" and "Wenckebach" techniques.

Another form of A-V or dual chamber pacer that has been utilized is the sequential pacemaker (DVI), which paces both the atrium and the ventricle with an appropriate A-V delay which is timed by the pacemaker. A number of commercial pacemakers have been introduced which are programmable to these and other known pacing modes. Each of the various operating modes is particularly adapted to certain circumstances that may arise in a given patient.

Since the dual sense-dual pace DDD pacemaker became commercially available, it has gained favor for the reason that it compensates for many of the disadvantages of other pacemaker modes. The classic DDD pacemaker is described in U.S. Pat. No. 4,920,965, Funke et al., in some detail. See also U.S. Pat. Nos. 4,539,991 and 4,554,921, incorporated herein by reference, which disclose other forms of DDD-type pacemakers.

More recently, the DDDR pacemaker has come to prominence. In this type of pacemaker, there is provided one or more sensors which enable the pacemaker to be rate responsive, such that the pacing interval, or escape interval, is varied as a function of one or more sensed rate-indicating parameters, rather than being fixed at a programmed value. In the DDDR pacemaker, both atrial and ventricular natural beats may occur so long as they occur prior to the respective rate responsive escape interval. See U.S. Pat. Nos. 4,467,807 and 4,951,667, which are illustrative of dual chamber rate responsive pacemakers.

There have also been disclosed multi-mode pacemaker designs having means for switching modes in response to changing patient conditions. Most dual chamber pacemakers are programmable to distinct modes, or switch automatically from one mode to another under certain prescribed conditions. See, for example, U.S. Pat. No. 4,527,568, and U.S. Pat. No. 4,920,965. However, there remains a substantial need in the pacing art for sensing the conditions under which a dual chamber pacemaker can or should be controlled to change mode, and for providing optimum flexibility for blending two or more modes of operation. Thus, instead of forcing the pacer to operate in a distinct mode until patient history enables switching to another distinct mode, the pacer would optimally be enabled to react on a cycle-to-cycle basis to sensed events. For example, while it is desirable to synchronize a delivered ventricular stimulus to a sensed atrial signal whenever possible, at the same time the pacemaker should be controlled to adopt another more optimum response whenever desired. Thus, if an atrial sensed beat occurs at too high a rate, or if retrograde conduction is determined, the pacemaker should have maximum flexibility for responding to this situation.

Reference is made to U.S. Pat. No. 5,247,930, assigned to the assignee of this invention, and incorporated herein by reference. This patent discloses a dual chamber pacing system which provides improved physiological synchronous tracking of atrial beats, and a means for continuously determining a physiological rate. The physiological rate normally tracks sensed atrial signals, but does not follow atrial signals found to be non-physiological. Thus, as long as the atrial signals are physiological, the "phys rate" is substantially equal to the sensed atrial rate. The referenced system establishes dynamic decision rates which are coupled to the physiological rate, including a dynamic tracking limit (DTL) and a dynamic pacing limit (DPL), which two limits define a physiological range. The dynamic range permits the pacemaker to adapt operation to varying atrial rates, and continue tracking a wider overall range of physiological atrial signals.

In the system of the referenced patent, the dynamic pacing limit is a son of flywheel rate, and represents the rate at which pace pulses are delivered in the absence of physiological atrial rates that can be synchronized. For example, the dynamic pacing limit may be maintained at 15 ppm below the phys rate as long as physiological atrial signals are sensed. However, if a real tachycardia situation occurs, the pacer responds with asynchronous pacing, i.e., the ventricle is paced without relation to the atrial senses. When this happens, it is necessary to decrement the flywheel rate, or DPL. In the referenced system, this is done by decrementing phys rate (along with DPL) until both reach the lower rate limit (LRL), or the sensor rate, whichever is higher.

However, a problem occurs in that not all disturbances are of a nature that the phys rate and the decision rates should be decremented down toward LRL. In particular, it has been found that it is desirable not to change the phys rate, and consequently the DTL, upon short disturbances. Thus, in event that there has been a stable normal sinus rate within the physiological band, and then there occurs a short disturbance such as a few PAC's or several undersensed beats in a VDD, it is desirable not to drop the entire physiological band. If the phys rate is decremented immediately toward LRL, carrying DTL with it, then when the stable normal sinus rate reappears, it might be outside (above) the physiological band, such that the pacemaker could not track it. There thus remains a substantial need in dual chamber pacemakers which dynamically adapt to a patient's physiological rate, to optimally react to short term disturbances of the sensed atrial rate, enabling the pacemaker to more quickly provide a synchronous response to a reappearing physiological sinus rate.

SUMMARY OF THE INVENTION

It is an object of this invention to provide a dual chamber pacing system which delivers synchronous ventricular pacing in response to physiological atrial signals, and which delivers ventricular pace pulses in an async mode in the absence of physiological atrial signals that can be tracked. The pacemaker of this invention has a dynamic pacing rate, or flywheel rate which tracks the physiological atrial rate, and which is normally decremented toward a lower rate limit when the pacemaker goes into an async mode. The dynamic tracking limit is decremented along with a flywheel rate, thereby decreasing the capability of tracking physiological atrial signals which may reappear at higher rates. The improvement provided by this invention meets the need of enabling the pacemaker to more quickly resume tracking of physiological atrial signals when they reappear after short disturbances, and in particular to be able to track atrial signals near the high limit of the physiological range of signals that can be tracked.

In accordance with the object of providing improved physiological synchronous tracking of atrial signals following short disturbances such as caused by PAC's or undersensed beats in a VDD mode, a first embodiment of the system of this invention provides that the dynamic tracking limit is maintained, or frozen for some duration following initiation of asynchronous pacing. The pacemaker establishes a dynamic pacing rate, or flywheel rate, having a predetermined relation to the rate of sensed physiological atrial signals, which flywheel rate is decremented when and as asynchronous paces are delivered due to loss of atrial signals that can be tracked. The pacemaker also maintains a dynamic tracking limit which is normally coupled to the sensed physiological atrial rate, which enables tracking sensed atrial signals within a range above the physiological rate. Upon the occurrence of asynchronous pacing, the physiological rate, dynamic tracking limit, and dynamic pacing limit are all maintained substantially constant for some number of cycles, before being decremented. In another embodiment, phys rate, dynamic tracking limit and dynamic pacing rate are decremented at the initiation of asynchronous operation, but the pacemaker remembers the dynamic tracking limit at this moment; when and if physiological atrial signals reappear at a rate above the decremented tracking limit but below the remembered tracking limit, then phys rate, dynamic pacing limit and dynamic tracking limit are incremented upward until tracking is resumed.

BRIEF DESCRIPTION OF THE DRAWINGS

FIGS. 3A–3D describe the primary operations and logic structure of the pacemaker of this invention. Specifically.

DESCRIPTION OF THE PREFERRED EMBODIMENTS

Figure 1:
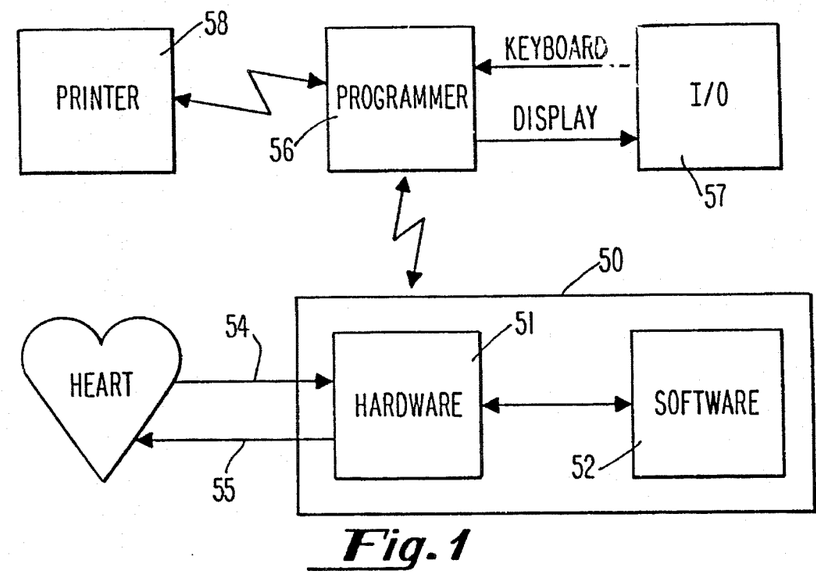
FIG. 1 is a block diagram of the overall system of the invention, showing the environment in which the pacemaker operates.

The pacing system of this invention is preferably software-based, i.e., the software controls functions through hardware, as illustrated in FIG. 1. Referring specifically to FIG. 1, the pacemaker 50 is shown as having a component hardware portion 51 and a software portion 52, the two portions being interconnected. The software is parameter-driven, i.e., there are numerous parameters that control the pacing behavior, diagnostic functions, etc. The hardware is interconnected with the patient's heart by one or more electrodes 55, and one or more sensor connections 54. As is well understood in the art, for a dual chamber pacemaker, there are generally two leads, an atrial lead and a ventricular lead, each lead having at least one electrode, unipole or bipole, positioned in the heart. The line 54 is illustrated as leading to the heart, as in a QT-type sensor arrangement, but may be attached to the outside case of the pacemaker or may couple to any other available sensors for sensing body parameter information used in rate responsive pacing systems. Further, in the preferred embodiment of the pacing system of this invention, sensor link 54 may comprise a pair of sensors, e.g., QT plus activity, as set forth in U.S. Pat. No. 5,065,759.

As further illustrated in FIG. 1, the pacer 50 is in telemetric communication with a programmer 56. The user can select parameters and program them through programmer 56, and can also interrogate parameter and diagnostic data from the implanted pacemaker. Interrogated information from the pacer can be coupled by telemetry directly to a printer 58. Input/output devices 57 are used to input information by the user to the programmer, or to display information received by the programmer from the pacemaker.

Figure 2:
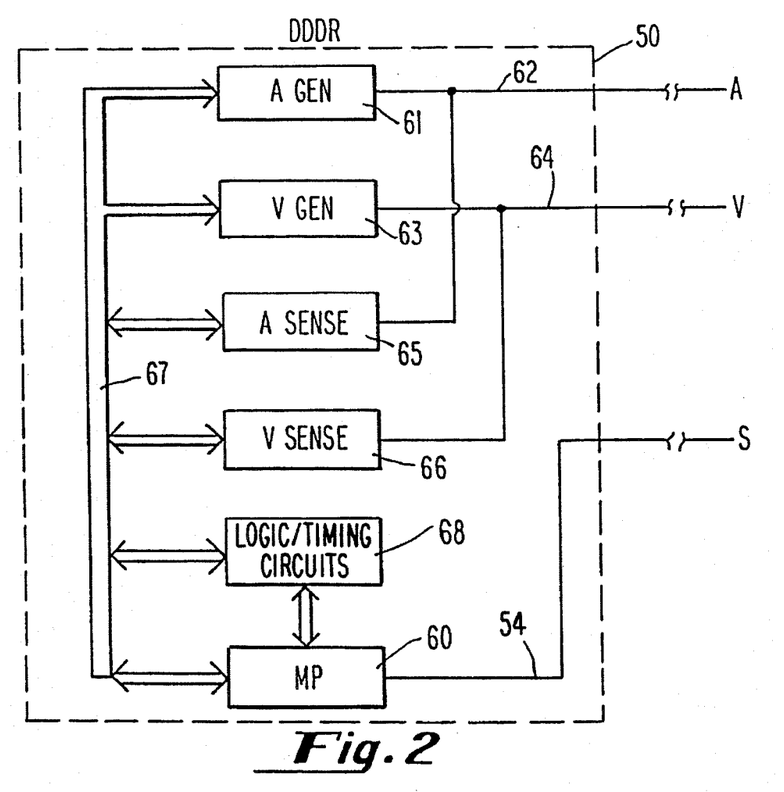
FIG. 2 is a block diagram which illustrates basic components of the pacemaker of this invention, together with leads and a sensor for delivering signals to and/or receiving signals from the patient.
Figure 9:
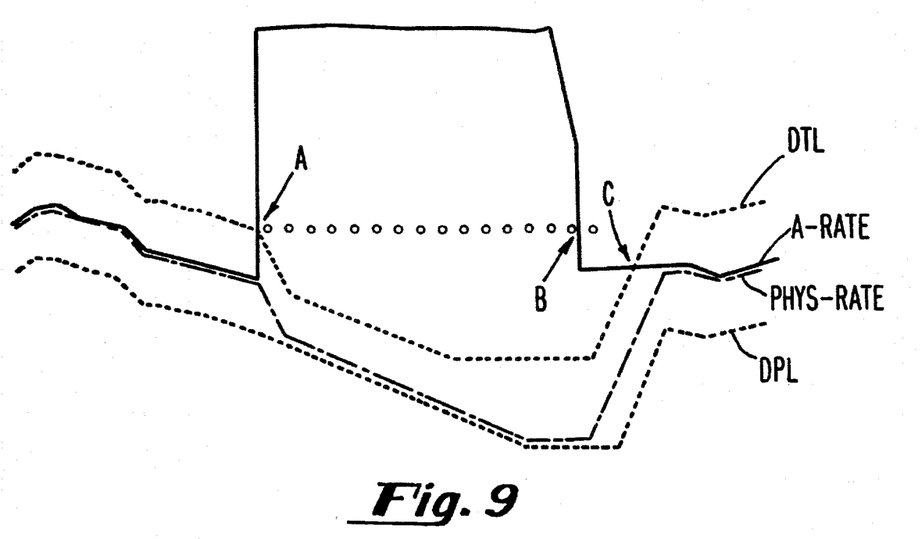
FIG. 9 is a rate diagram illustrating a second embodiment of the invention, where the pacemaker remembers the value of the dynamic tracking limit at the start of the tachy episode, and provides for a smooth and relatively quick return to synchronous operation after the atrial rate reappears at substantially its value just prior to the tachy episode.

Referring to FIG. 2, there is shown a basic block diagram of primary hardware components of a DDDR pacer 50. An atrial generator 61 is shown, having an output connected to lead 62 which communicates with the patient's atrium. An A-sense amplifier 65 is illustrated also connected to atrial lead 62. A ventricular generator is illustrated which is connected to the patient's ventricle through lead 64. V-sense amplifier 66 is also connected to lead 64, to receive and sense signals from the patient's ventricle. In one embodiment of this invention which preferably incorporates QT rate control, V-sense block 66 also includes means for picking out and determining the timing of the evoked T wave. Generators 61 and 63 and sense blocks 65 and 66 are interconnected with microprocessor system 60, which microprocessor has software which is parameter-driven to control the operation of the hardware units. Microprocessor system 60 may be interconnected with hardware logic and/or timing circuits 68. As affects the scope of this invention, the degree to which software supplants hardware, or vice versa, is a matter of design choice. Thus, for the many timing functions that are carried out in the pacing system of this invention, it is to be understood that the microprocessor may have built in timing circuits, or suitably may control external hardware timer circuits. Software control of pacing function is well known in the art, such that the following detailed discussions of software routines enable one of ordinary skill in this art area to design a system for carrying out the functions within the scope of the invention. Data inputted from programmer 56 is stored in memory associated with microprocessor. Likewise, the tinting diagrams of FIGS. 5B and 9 are the equivalent of software routines in disclosing the several embodiments.

Still referring to FIG. 2, there is shown a sensor S indicated as providing an input to microprocessor system 60. Sensor S represents one or more sensors for monitoring one or more body parameters to provide an indication of desired pacing rate. The pacemaker of this invention may be rate responsive in the manner as described in the referenced U.S. Pat. No. 5,247,930.

Figure 3A:
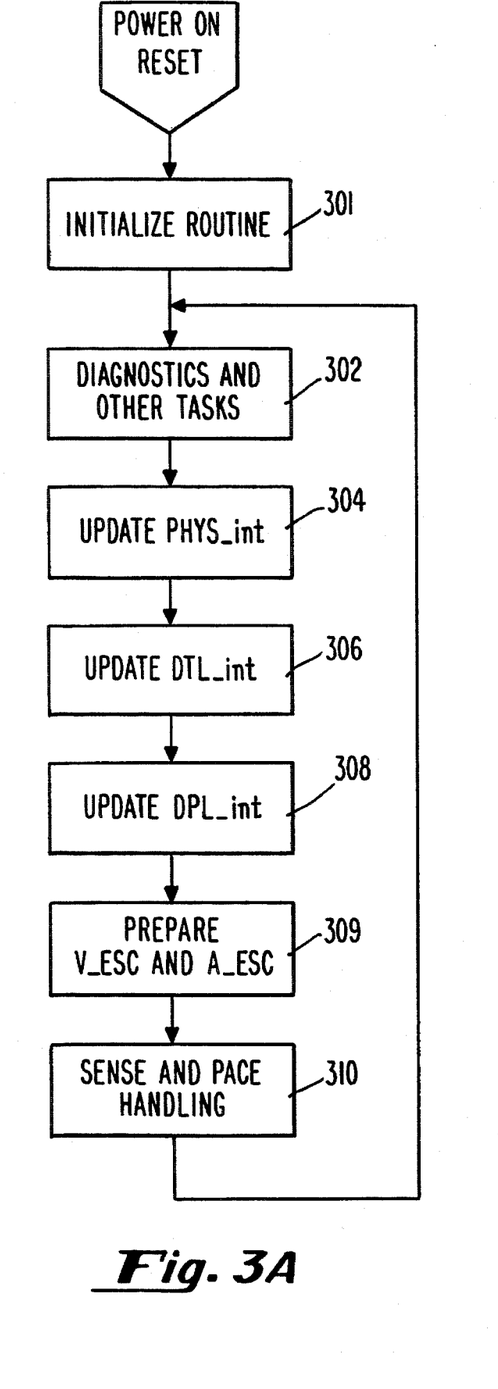
FIG. 3A is a flow diagram showing the main sequential steps carried out each cycle.

Referring now to FIG. 3A, there is shown a flow diagram of the main logical steps taken by the pacemaker of this invention. The basic rules of operation are as follows:

For DDD(R) mode, VEsc=DPLint and AEsc=VEsc–AV delay.

For VDD(R) mode, VEsc=DPLint, and AEsc is not started. Note also that the two escape intervals may be varied for other purposes, such as hysteresis.

Entering the routine, the variables are first initialized at 301. At 302, the pacemaker performs any diagnostic or other tests which are programmed. At block 304, the pacemaker updates physint which, as discussed above, is a measure of the rate of physiological atrial signals. Of course, under some conditions there may be no change in physint in any given cycle. At block 306, the dynamic tracking limit interval (DTLint), is updated in coupled relation to phys int. Likewise, at 308, DPLint is updated in coupled relation to physint. Reference is made to U.S. Pat. No. 5,247,930, which gives a detailed discussion of these decision rates. At block 309, the pacemaker prepares the two escape intervals VEsc and AEsc, and waits. Block 310 generally indicates sense and pace handling, i.e., how the pacemaker responds to a sensed event or timeout of one or the other escape intervals.

Figure 3B:
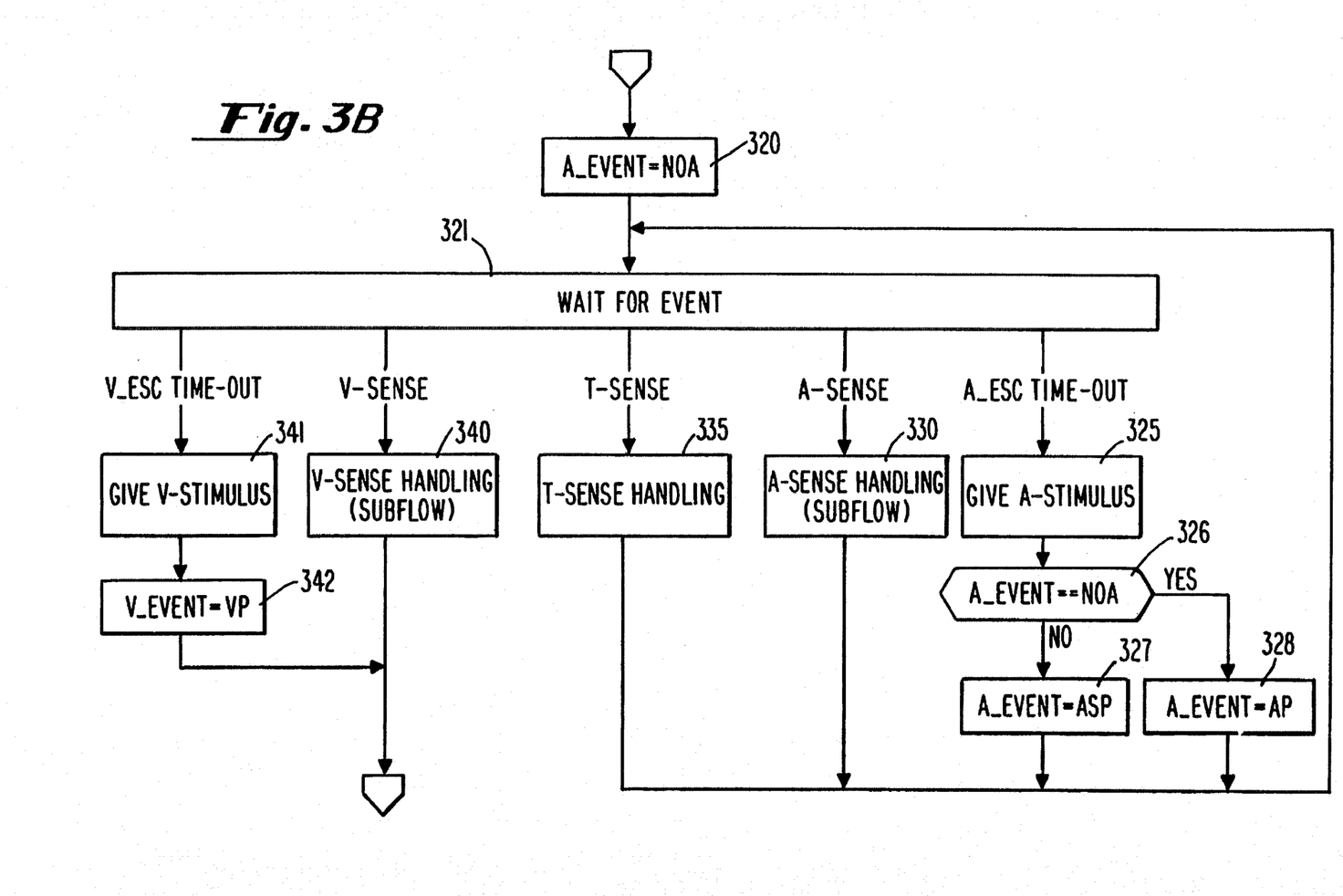
FIG. 3B is a flow diagram of sense and pace handling, i.e., how the pacemaker responds to an atrial sense (AS) or ventricular sense (VS), and when it delivers an atrial pace pulse (AP) or ventricular pace pulse (VP)

Referring now to FIG. 3B, there is shown a more detailed flow diagram of the sense and pace handling. At block 320, it is indicated that this routine is entered when no A event has yet occurred during the cycle. At block 321, the pacemaker waits for an event. As indicated, there are five possibilities. Proceeding from right to left, there can be a timeout of the atrial escape interval, AEsc, in which case the pacemaker goes to block 325 and delivers an A-stimulus. The pacemaker then determines at 326 whether there had been no prior atrial event. If yes, such that NOA is interpreted, at block 328 the pacemaker records the event as an AP. However, if it was not an NOA, the pacemaker branches to block 327 and records the A event as an ASP. Returning to block 321, there can be an A-sense, in which case the pacemaker goes to block 330 and proceeds with A-sense handling, which is set forth in more detail in FIG. 3C. For a QT rate responsive pacemaker, the event can be a T-sense, in which case the pacemaker goes to block 335 and carries out the T-sense handling. The event may be a V-sense, in which case the pacemaker goes to block 340 and handles the V-sense, which is described in more detail in the flow diagram of FIG. 3D. Or, there can be timeout of the V Esc, in which case the pacemaker goes to block 341 and delivers the V-stimulus, following which the pacemaker records that the Vevent was a ventricular pulse (VP) at block 342.

Note that FIG. 3B is simplified in the sense that it gives only the basic steps for a VDD(R) and DDD(R) mode, and does not include such considerations as adjusting for the rate responsive sensor input.

Figure 3C:
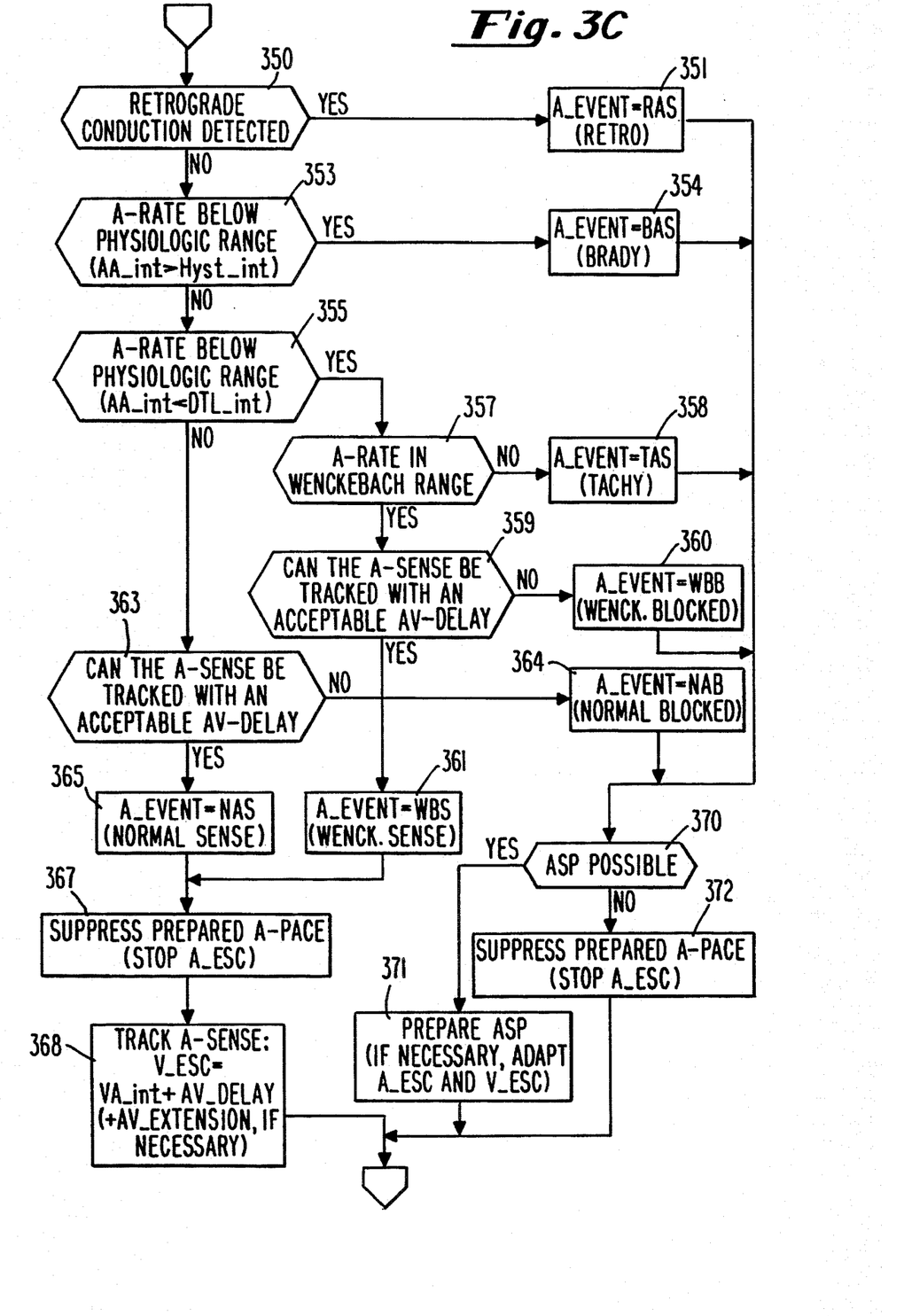
FIG. 3C is a more detailed flow diagram of the subroutine for A-sense handling.

Referring now to FIG. 3C, there is shown a more detailed flow diagram of A-sense handling, or how the pacemaker responds to a sensed atrial signal. At block 350, it is determined whether retrograde conduction has been detected. If yes, the routine branches to block 351, and identifies the event as an RAS, or retro atrial sense. The routine then goes to block 370 and determines whether delivery of an ASP is possible. If yes, the routine goes to block 371 and prepares an ASP, adapting AEsc and VEsc as might be required. If no ASP is possible, the prepared A-pace is suppressed at block 372, such that no atrial pace is delivered.

Returning to block 350, assuming there is no retrograde conduction, the pacemaker goes to block 353 and determines whether the atrial rate is below the physiological range, i.e., whether there has been a brady event. As indicated, this is determined by comparing the AAint with Hyst int, where Hystint equals DPLint+AHyst, the last factor representing hysteresis below the pacing rate. If the A-rate is below the physiologic range, the pacemaker goes to block 354 and identifies the atrial event as a BAS. However, if it is not below the physiological range, the pacemaker goes to block 355 and determines whether the rate is above the physiological range, i.e., AAint<DTLint. If yes, the routine branches to block 357 and determines whether the atrial rate is within the Wenckebach range. If no, at 358 the atrial event is identified as a TAS. However, if the atrial rate is within the Wenckebach range, the routine goes to block 359 and determines whether the A-sense can be tracked with an acceptable AV-delay. If no, the routine goes to block 360 and identifies the atrial event as a WBB, indicating Wenckebach blocked. However, if the A-sense can be tracked, the routine goes to block 351 and identifies the atrial event as a WBS, meaning a Wenckebach sense. Thereafter the routines goes to block 367.

Returning to block 355, if the answer is no, this means that the atrial rate is within the physiological range, i.e., between DTL and DPL, taking into account any hysteresis. The routine then goes to block 363 and determines whether the A-sense can be tracked with an acceptable AV delay. If no, meaning that the resulting ventricular pace would be delivered at too high a rate, the pacemaker branches to block 364 and identifies the atrial event as an NAB, i.e., a normal atrial event blocked. However, if it can be tracked, the routine goes to block 365 and identifies the atrial event as NAS, normal atrial sense. Then at block 367 the pacemaker suppresses the prepared atrial pace, and at block 368 the pacemaker tracks the atrial sense, resetting the ventricular escape interval to VAint+AVdelay, adding an AVExtension if necessary.

Figure 3D:
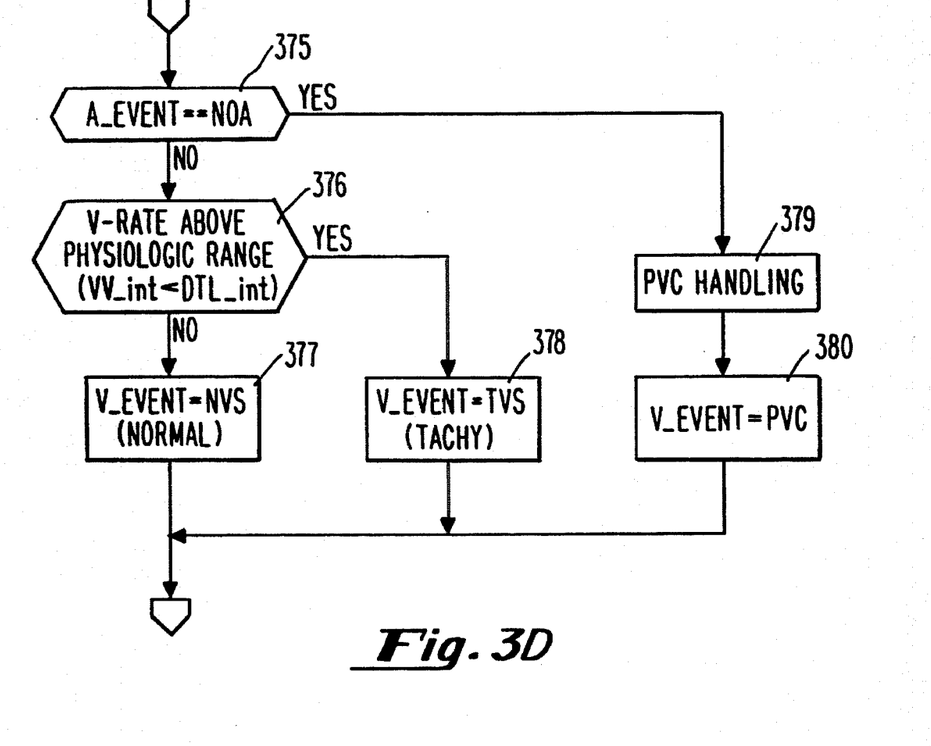
FIG. 3D is a more detailed flow diagram of the subroutine for V-sense handling.

Referring now to FIG. 3D, there is shown a flow diagram for V-sense handling, i.e, how the pacemaker responds to a V-sense. At block 375, it is determined whether no atrial event has occurred yet, i.e., NOA. If yes, this means that there has been a PVC, and the pacemaker branches to block 379 and carries out the handling in response to a PVC. Then at block 380 the pacemaker identifies the Vevent as a PVC. However, if at 375 it is determined that there has been an intervening atrial event, the routine goes to 376 and determines whether the ventricular rate is above the physiological range, i.e., VVint<DTLint. If yes, the routine branches to 378 and identifies the Vevent as TVS, i.e., tachy. However, if the answer is no, the routine goes to block 377 and identifies the V event as a normal ventricular sense (NVS).

Figure 4:
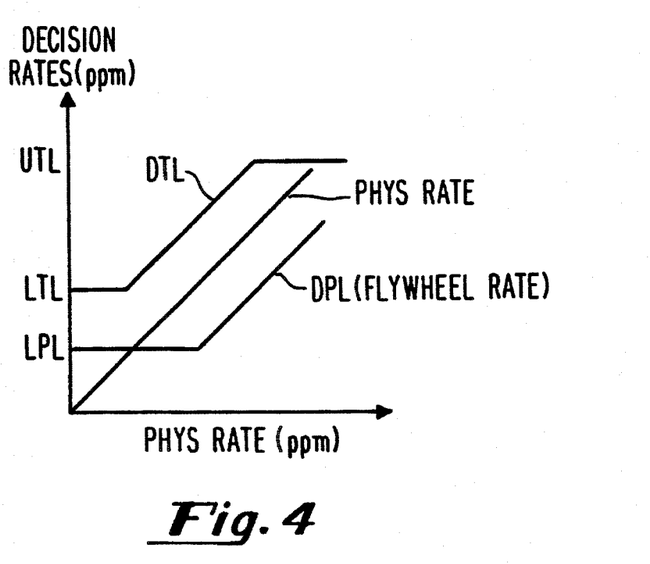
FIG. 4 represents curves illustrating dynamic decision rates as a function of physiological rate.

Referring specifically to FIG. 4, there is shown a variation of the three decision rates as a function of phys rate. Phys rate, which tracks physiological atrial signals, is the reference to which the dynamic tracking limit is coupled between a lower tracking limit (LTL) and an tipper tracking limit (UTL). The dynamic pacing limit tracks between a lower pacing limit (LPL) and phys rate, the difference between phys rate and DPL being the flywheel distance. However, as seen in FIGS. 5A and 9, when the atrial rate is not physiological, these decision rates are decremented downward, with phys rate and DPL both going to the lower pacing limit.

Figure 5A:
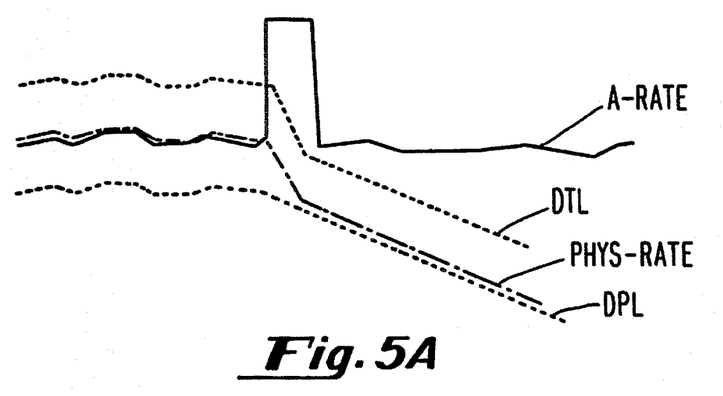
FIG. 5A is a rate diagram illustrating how tracking can be lost following a short episode of tachycardia which results in asynchronous operation, following which the sensed atrial rate returns to its prior level but remains above the dynamic tracking limit.
Figure 5B:
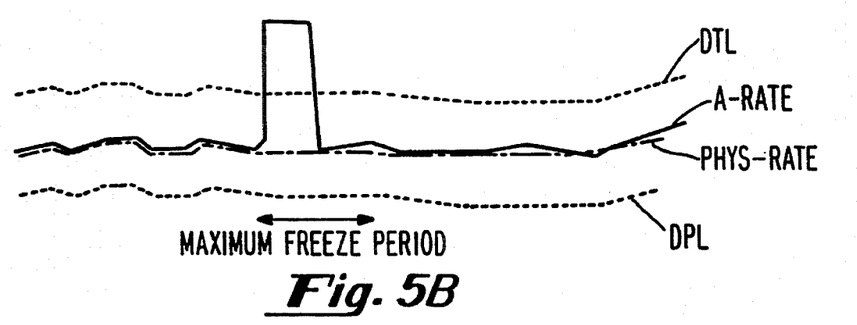
FIG. 5B illustrates how the "freeze" operation provided by this invention enables an immediate return to synchronous operation following the end of the short tachy episode.

FIG. 5A is a rate diagram which represents a short occurrence of atrial tachycardia, and how the decision rates vary without the improvement of this invention. As seen, the physrate is initially substantially tracking the physiological atrial rate, with DTL coupled at some rate increment above and DPL coupled at some rate increment below. When the atrial rate jumps up above DTL for a period of time, indicating a short episode of A-tachy, the pacemaker goes into an async mode. Under these circumstances, physrate, DTL and DPL both flywheel down, as shown. This is done because it is desired that the asynchronous pacing be carried out at a lower rate. Note that physrate ramps down quickly to the pacing rate (DPL), and DTL likewise ramps down in coupled relation to the physrate. As illustrated here, when the tachy episode is over, and the atrial rate returns to substantially its value before the tachy episode, the atrial rate is now above DTL, and is thus outside the physiological range. This means that tracking is not possible, and the pacer stays in the async mode. Under these circumstances, it is a matter of chance when the pacemaker might be able to return to synchronous pacing.

The improvement of this invention is illustrated in FIG. 5B, wherein the pacemaker control is modified by instituting a freeze period so as to be able to resume tracking if the tachycardia episode is short. As illustrated here, the tachycardia interval is about eight cycles, while the freeze period is indicated as being longer. Physrate, as well as DTL and DPL, are frozen, or maintained constant, during the tachy episode, such that when the atrial rate returns to its previous value, it again falls within the physiologic range. Under these circumstances, the pacer returns to the sync mode immediately upon termination of the tachy period. This illustrates a first embodiment whereby the pacemaker maintains the value of DTL at the start of the async episode, and is thereby able to classify the atrial signals as physiologic when the short tachy episode terminates, and quickly resume synchronous pacing.

Figure 6:
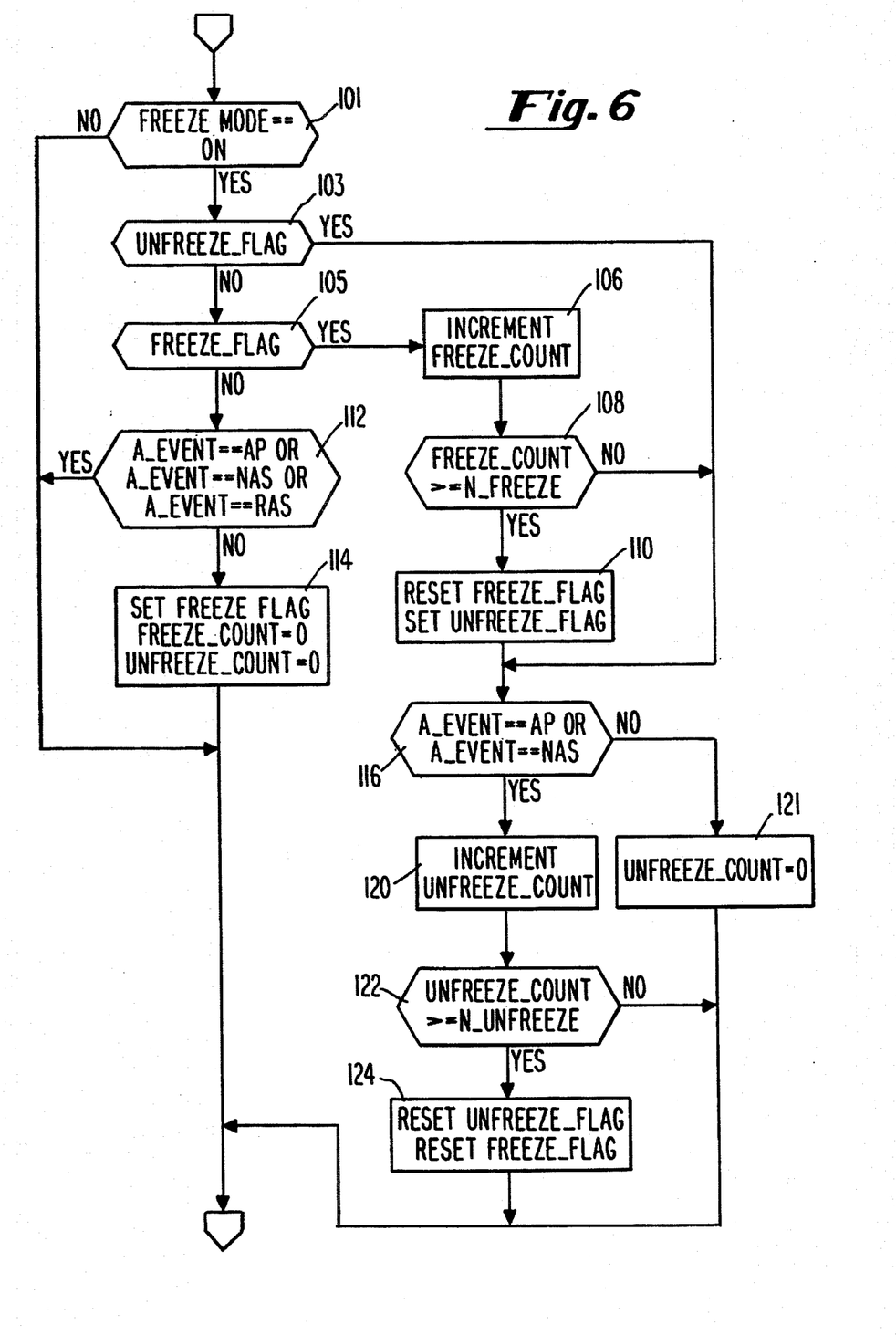
FIG. 6 is a flow diagram representing the logic analysis performed by the pacemaker of this invention in determining when and how the freeze function of the first embodiment operates.
Figure 7:
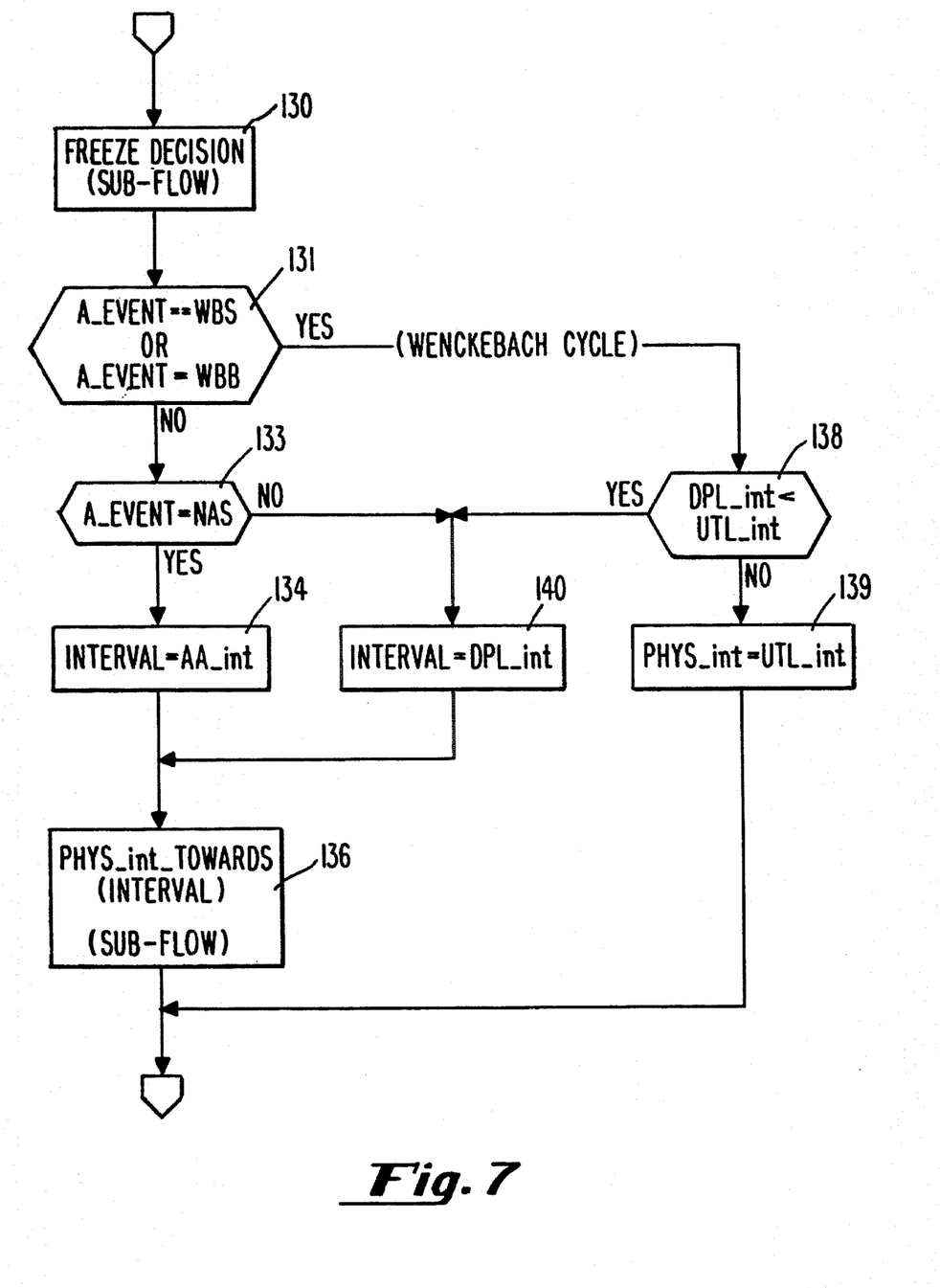
FIG. 7 is a flow diagram illustrating the logic of updating physiological interval, or phys rate in the pacemaker of this invention.
Figure 8:
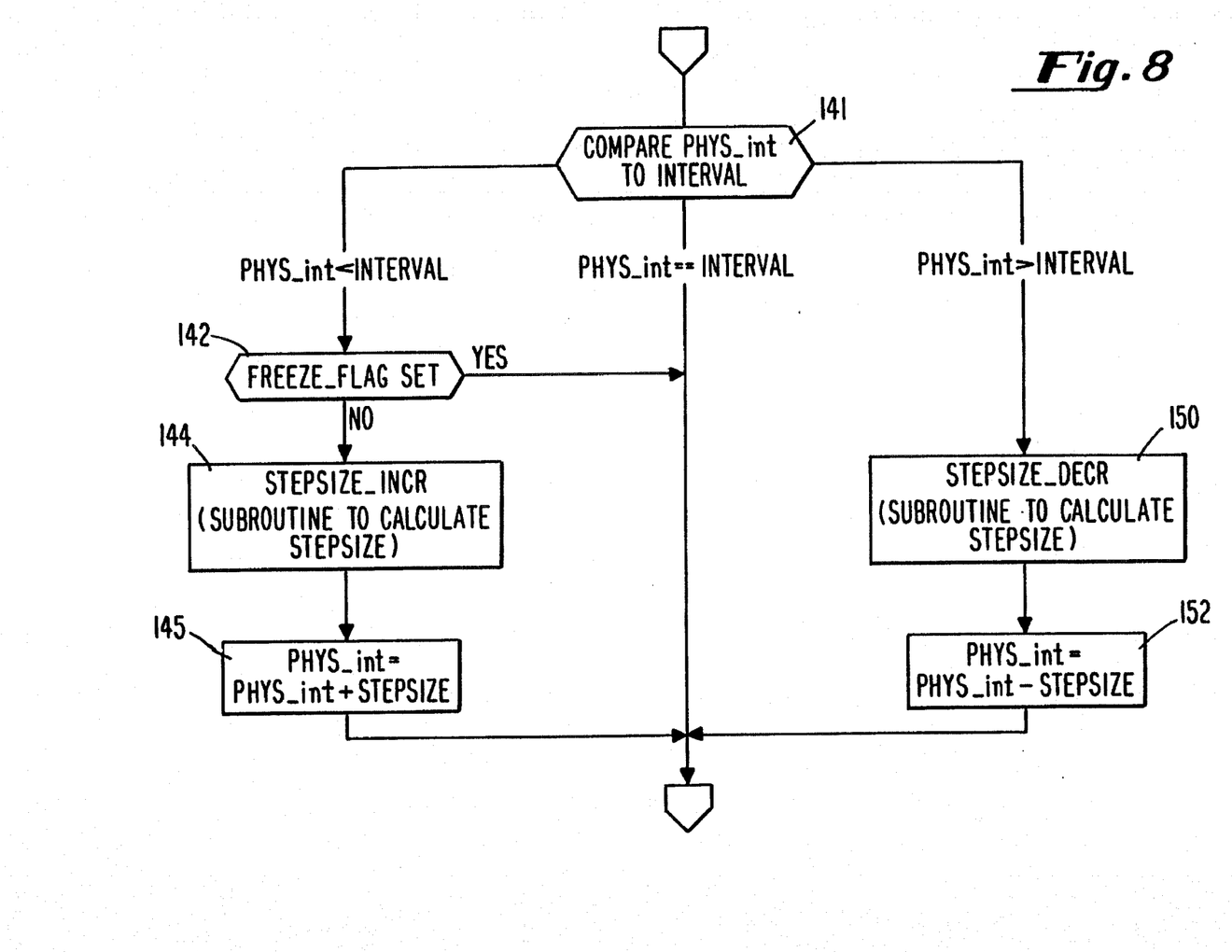
FIG. 8 is a flow diagram showing the steps taken by the pacemaker of this invention in incrementing or decrementing the phys rate.

The routines of FIGS. 6–8 illustrate the "freeze" function improvement. Referring specifically now to FIG. 6, at 101 the pacemaker determines whether the freeze mode is on. If it is not, this subroutine is exited directly. However, assuming freeze mode has been programmed on, the routine branches to 103 and determines whether the unfreeze flag is set. If no, the routine proceeds to block 105 and determines whether the freeze flag is set. If no, the routine goes to block 112 and determines whether there has been an atrial pace pulse, a normal atrial sense, or an RAS. If yes, the routine exits. If no, the routine branches to block 114. At block 114, which is reached when the pacemaker has first gone into an asynchronous mode or has delivered an atrial sync pulse, the freeze flag is set, initiating the freeze condition. A counter which is indicated as Freeze Count is set equal to zero, and likewise a counter indicated as Unfreeze Count is set equal to zero, and the routine then exits.

Returning to block 105, if the freeze flag has been previously set (at block 114), at the next cycle the routine branches to block 106 and increments the freeze count. Next, at 108, the pacemaker determines whether the freeze count has reached a predetermined number, illustrated as N-freeze. For example, N may be set to 8, but may be as high as 32. If no, the routine branches to block 116. However, if the freeze count has reached N, the routine goes from block 108 to block 110 and resets the freeze flag. At the same time, the unfreeze flag is set, initiating a count out of a predetermined number of cycles before the pacemaker permits the freeze flag to be set again.

At block 116, the pacemaker checks to see whether the A event has been an AP or NAS. If no, the routine branches to block 121 and sets the unfreeze count to zero. However, if yes, this means that the last cycle had a synchronous pulse, so the routine branches to block 120 and increments the unfreeze count. Then, at block 122, the unfreeze count is compared to a predetermined number, illustrated as N-unfreeze, e.g., 3. If the unfreeze count has not reached N unfreeze, the routine exits. However, if it has, the routine goes to block 124 and resets the unfreeze flag and the freeze flag. The pacemaker is then enabled to recommence the freeze condition.

Referring now to FIG. 7, there is shown a subroutine for updating the phys interval, corresponding to the phys rate. Following the freeze decision routine of FIG. 6, indicated at block 130, the routine goes to 131 and determines whether the atrial event was a Wenckebach event, WBS or WBB. If no, at 133 the routine determines whether there has been a normal atrial sense (NAS). If yes, at block 134 the variable "interval" is set equal to the AA time of the last cycle, i.e., the time between atrial signals. Following this, the routine goes to the next subroutine at block 136, illustrated in FIG. 8, for determining the new value of physint.

Returning to 131, if there has been a Wenckebach event, the routine goes to 138 where the pacemaker determines whether the dynamic pacing limit interval is less than the upper tracking limit interval. If no, at 139 the phys interval is set equal to the upper tracking limit interval. If the answer at 138 is yes, the routine goes to block 140 and sets the interval variable equal to the dynamic pacing limit interval. Likewise, if the answer at 133 is no, meaning that the A event was an A pace or an asynchronous A-sense, or no atrial event, interval is set to DPL int at block 140.

Referring to FIG. 8, at 141, the present value of phys interval, corresponding to the last calculated phys rate, is compared to the "interval" value determined in FIG. 7. If phys interval is less than the interval value, the routine goes to block 142, and determines whether the freeze flag is set. If yes, this routine exits, such that there is no change in the phys interval, i.e., phys interval is "frozen." However, if the freeze flag is not set, the routine goes to block 144, and determines a stepsize for incrementing phys interval (decreasing phys rate). This is done by a separate subroutine, not shown. In the simplest case, the stepsize can be a fixed programmable value. Then, at 148 phys interval is set equal to the prior value of physint plus the stepsize. Returning to 141, if phys interval is found to be greater than the interval value determined in FIG. 7, the routine branches to block 150 and determines from a subroutine the stepsize by which phys interval is to be decremented (phys rate increased). Then, at 152, phys interval is decremented by the determined stepsize. Note that if physint is found to be equal to the variable "interval" at block 141, there is no change and the routine is exited directly.

In reviewing FIGS. 6–8, along with FIG. 5B, it is seen that the pacemaker of this invention provides for freezing phys rate for up to N cycles following a first cycle that has an async V pulse. This also freezes DTL, such that a relatively high physiological rate that reappears within about N cycles can usually be tracked immediately. For N freeze=8 and N unfreeze=3, the pacemaker can unfreeze in less than eight cycles if three consecutive sync cycles are detected before eight cycles are counted out. The unfreeze feature, namely counting consecutive sync cycles following or during a freeze episode, prevents taking the pacer into the freeze mode too quickly after it has just been in the freeze mode, and can get it out more quickly. Note also that freeze can be exited after just four cycles if there is one async cycle followed by three synchronous cycles. This is helpful because it is desirable not to hold the pacemaker in the freeze function if there has been just one PAC or the like.

In the illustration of FIGS. 6–8, the phys rate, flywheel rate and tracking rate are all frozen during a freeze. This is one way of maintaining the value of DTL at the start of async operation. However, the routine may be modified in accord with the rate diagram shown in FIG. 9. As illustrated here, there is a long A-tachy period, or interval, during which the pacer goes into async mode. The A-tachy starts as indicated at A, where the atrial rate exceeds DTL and is interpreted by the pacemaker as A-tachy. At this point, the value of the then current DTL is copied and held in memory, as illustrated by the horizontal line of small circles. Instead of being frozen, physrate, DTL and DPL flywheel down, with DPL reaching a lower pacing limit before the end of the tachy period. When the tachy episode, which is indicated as lasting about fifteen cycles, is over, as indicated at B, the atrial rate drops below the remembered value of DTL. This comparison causes the pacemaker to ramp up physrate, DTL and DPL, e.g., they flywheel up as indicated by the rising lines. At the point indicated by C, the atrial rate is again within the physiological range, i.e., below DTL, and tracking can be resumed. The pacer thus returns to synchronous operation quickly after the end of the atrial tachycardia episode.

It is to be understood that variations of this second embodiment combined with the first embodiment may be made within the scope of this invention as claimed. Thus, it may be desirable to freeze physrate and the decision rates for just a few cycles, and then flywheel down, remembering the value of DTL where it was briefly frozen at the start of async operation. Note also that it is desirable to "forget" or drop the remembered value of DTL, or representation of tracking limit, after a certain elapsed time or number of pacemaker cycles, after which the maintained value would become irrelevant. This can be done by decrementing the remembered DTL value very slowly until it reaches the current value of DTL; by making the remembered value of DTL equal to DTL after a certain time or number of beats; or by clearing the remembered value of DTL after a certain time or number of beats.

What is claimed is:

1. A dual chamber pacemaker system for pacing a patient, having stimulus means for generating and delivering pace pulses to the patient's ventricle, atrial sensing means for sensing atrial signals from the patient's atrium, means for determining a measure of atrial rate from said atrial signals, and control means for controlling said stimulus means, wherein said control means further comprises:

DTL means for establishing a dynamic tracking limit above said measure of atrial rate and having a coupled relation to said measure of atrial rate, and DPL means for establishing a dynamic pacing limit varying with said measure of atrial rate, sync means for controlling said stimulus means to provide ventricular pace pulses in timed relation to sensed physiological atrial signals which occur at rates below said dynamic tracking limit and above said dynamic pacing limit, and async means for controlling said stimulus means to provide async pulses at said dynamic pacing limit in the absence of sensed physiological atrial signals having rates between said dynamic pacing limit and said dynamic tracking limit, adjust means for decrementing said physiological rate, said dynamic tracking limit and said dynamic tracking limit when said async means controls said stimulus means to provide async pulses, and said adjust means further having freeze means for holding said dynamic tracking limit and said dynamic pacing limit substantially unchanged for at least a plurality of cycles following an async pulse, thereby delaying said decrementing.

2. The pacemaker system as described in claim 1, wherein said freeze means holds said dynamic pacing limit and said dynamic tracking limit substantially unchanged for N cycles following an async pulse, where N is in the range 1–32.

3. The pacemaker system as described in claim 2, further comprising unfreeze means for disabling operation of said freeze means for a predetermined time following a freeze episode.

4. The pacemaker system as described in claim 3, wherein said unfreeze means further disables said freeze means before N cycles when there have been intervening synchronous cycles.

5. The pacemaker system as described in claim 1, wherein said adjust means decrements said dynamic tracking limit and said dynamic pacing limit by a determined stepsize each cycle so long as asynchronous operation continues, down to predetermined lower limits.

6. A dual chamber pacemaker system for pacing a patient, having stimulus means for generating and delivering pace pulses to the patient's ventricle, atrial sensing means for sensing atrial signals from the patient's atrium, rate means for determining the rate of sensed atrial signals, and control means for controlling pulse generation by said stimulus means, wherein said control means further comprises:

tracking limit means for establishing a dynamic tracking limit (DTL) representative of a rate above said rate of sensed atrial signals and having a first relation to said rate of sensed atrial signals, and flywheel means for establishing a flywheel rate below said rate of atrial signals and having a second relation to said rate of sensed atrial signals, sync means for controlling said stimulus means to deliver ventricular pace pulses in timed relation to sensed atrial signals which occur at a rate below said DTL and above said flywheel rate, async means for controlling said stimulus means to deliver async pulses at said flywheel rate in the absence of sensed atrial signals having rates between said flywheel rate and said DTL, and async response means for holding said DTL rate and said flywheel rate substantially constant for at least a plurality of pacemaker cycles when async pulses are being delivered, and for decrementing said DTL rate and flywheel rate toward respective lower limits when async pulses continue to be delivered after said plurality of cycles.

7. The pacemaker system as described in claim 6, wherein said plurality of pacemaker cycles is a number (N) in the range of 1–32.

8. The pacemaker system as described in claim 6, wherein said async response means comprises means for remembering the DTL rate just before start of delivering async pulses.

9. The pacemaker system as described in claim 8, further comprising means for incrementing said DTL and flywheel rates when atrial signals are sensed at rates below said remembered DTL rate.

10. A dual chamber pacemaker system for pacing a patient, having stimulus means for generating and delivering pace pulses to the patient's ventricle, atrial sensing means for sensing atrial signals from the patient's atrium, means for determining atrial rate from said atrial signals, phys means for determining a physiological rate as a function of atrial rate and control means for controlling said stimulus means, wherein said control means further comprises:

tracking means for establishing a tracking rate limit, sync means for controlling said stimulus means to provide sync pace pulses in timed relation to sensed atrial signals which occur at rates below said tracking rate limit, and async means for controlling said stimulus means to provide async pulses in the absence of sensed atrial signals below said tracking rate limit;

maintaining means for maintaining a substantial representation of said tracking rate limit when async pulses are first provided; and re-sync means for enabling providing of sync pace pulses following the occurrence of atrial signals sensed at a rate below said maintained tracking rate limit.

11. The pacemaker system as described in claim 10, wherein said re-sync means comprises further means for enabling providing of a sync pace pulse following the first atrial signal which is sensed at a rate below said maintained tracking rate limit.

12. The pacemaker system as described in claim 10, wherein said maintaining means comprises freezing means for freezing said tracking rate limit and said physiological rate for up to $N_1$ cycles, and unfreeze means for disabling operation of said freeze means for $N_2$ cycles.

13. The pacemaker system as described in claim 10, comprising freeze means for freezing said tracking rate and said physiological rate for a first predetermined time and unfreeze means for disabling operation of said freeze means for a second predetermined time following a freeze episode.

14. The pacemaker system as described in claim 10, further comprising limiting means for limiting the validity of said maintained representation.

* * * * *

UNITED STATES PATENT AND TRADEMARK OFFICE
CERTIFICATE OF CORRECTION

PATENT NO. : 5,531,771
DATED : July 2, 1996
INVENTOR(S) : Johannes S. van der Veen et al.

It is certified that error appears in the above-indentified patent and that said Letters Patent is hereby corrected as shown below:

Col. 2, line 31, "son" should read --sort--.

Col. 5, line 37 should read --For DDD(R) mode, V_Esc = DPL_int, and A_Esc = V_Esc - AV_delay.--

Col. 5, line 40, should read --For VDD(R) mode, V_Esc = DPL_int, and A_Esc is not--

Col. 5, line 50, " DTLint " should read -- DTL_int --

Col.5, line 51, "(DPLint)" should read --(DPL_int)--

Col. 5, line 55, "VEsc and AEsc" should read --V_Esc and A_Esc--

Col.5, line 65, "AEsc" should read --A_Esc--

Col. 6, line 12, "V" should read --V_--

Col.6, line 15, "Vevent" should read --V_event--

Col. 6, line 30, "AEsc and VEsc" should read --A_Esc-- and --V_Esc--

Col. 6, line 38, "AAint" and "Hyst" should read -- AA_int-- and --Hyst_--

Col. 6, line 39, "Hystint" should read --Hyst_int--; and "DPLint+AHyst" should read --DPL_int and $\overline{A}$_Hyst--

UNITED STATES PATENT AND TRADEMARK OFFICE
CERTIFICATE OF CORRECTION

PATENT NO. : 5,531,771
DATED : July 2, 1996
INVENTOR(S) : Johannes S. van der Veen et al.

It is certified that error appears in the above-indentified patent and that said Letters Patent is hereby corrected as shown below:

Col. 6, line 45, "Aaint<DTLint" should read --AA_int<DTL_int--

Col. 7, line 3, "VAint+AV delay, adding an AVExtension" should read --VA_int + AV_ delay, adding an AV_Extension--.

Col. 7, line 10, Vevent" should read --V_event--

Col. 7, line 15, "VVint<DTLint" should read --VV_int<DTL_int--

Col.7, line 37, Physrate" should read --phys_rate--

Col.7, line 42, "physrate" should read --phys_rate--

Col. 7, line 55, "Physrate" should read --Phys_rate--

Col. 8, line 51, "physint" should read --phys_int--

Col. 8, line 59, "A" should read --A_--

Col. 9, line 7, "physint" should read --phys_int--

Col. 9, line 13, "physint" should read --phys_int--

Col.9, line 44, "physrate" should read --phys_rate--

Col.9, line 49, "physrate" should read --phys_rate--

UNITED STATES PATENT AND TRADEMARK OFFICE
CERTIFICATE OF CORRECTION

PATENT NO. : 5,531,771
DATED : July 2, 1996
INVENTOR(S) : Johannes S. van der Veen et al.

It is certified that error appears in the above-indentified patent and that said Letters Patent is hereby corrected as shown below:

Col.9, line 59, "physrate" should read --phys_rate--

Signed and Sealed this

Twenty-second Day of April, 1997

BRUCE LEHMAN

*Commissioner of Patents and Trademarks*

*Attest:*

*Attesting Officer*